United States Patent [19]
Sheppard et al.

[11] Patent Number: 5,573,854
[45] Date of Patent: Nov. 12, 1996

[54] COMPOSITES MADE FROM MULTIDIMENSIONAL OLIGOMERS

[75] Inventors: Clyde H. Sheppard, Bellevue, Wash.; Hyman R. Lubowitz, Rolling Hills Estates, Calif.

[73] Assignee: The Boeing Company, Seattle, Wash.

[21] Appl. No.: 463,329

[22] Filed: Jun. 5, 1995

Related U.S. Application Data

[62] Division of Ser. No. 38,750, Mar. 26, 1993, Pat. No. 5,463,076, which is a division of Ser. No. 605, Jan. 5, 1987, Pat. No. 5,210,213, and a continuation-in-part of Ser. No. 810,817, Dec. 17, 1985, abandoned, which is a continuation-in-part of Ser. No. 726,258, Apr. 23, 1985, abandoned, which is a continuation-in-part of Ser. No. 519,394, Aug. 1, 1983, abandoned, and a continuation-in-part of Ser. No. 673,229, Nov. 20, 1984, Pat. No. 4,584,364, which is a continuation of Ser. No. 576,790, Feb. 6, 1984, abandoned, which is a continuation-in-part of Ser. No. 321,119, Nov. 13, 1981, abandoned, and a continuation-in-part of Ser. No. 536,350, Sep. 27, 1983, abandoned, which is a continuation-in-part of Ser. No. 519,394, Aug. 1, 1983, abandoned, and a continuation-in-part of Ser. No. 505,348, Jun. 17, 1983, Pat. No. 4,536,559, and a continuation-in-part of Ser. No. 651,826, Sep. 18, 1984, abandoned, which is a continuation-in-part of Ser. No. 536,350, Sep. 27, 1983, abandoned, and a continuation-in-part of Ser. No. 505,348, Jun. 17, 1983, Pat. No. 4,536,559.

[51] Int. Cl.$^6$ ............... C08J 5/24; B32B 31/04
[52] U.S. Cl. .............. 428/411.1; 428/361; 428/367; 428/368; 428/395; 428/396; 428/408; 428/423.1; 428/473.5; 428/474.4
[58] Field of Search ............ 428/411.1, 423.1, 428/473.5, 361, 367, 368, 395, 396, 408, 474.4; 548/435, 431, 433, 462, 465, 521

[56] References Cited

U.S. PATENT DOCUMENTS

| | | |
|---|---|---|
| H183 | 1/1987 | Karasz . |
| Re. 29,316 | 7/1977 | Bargain et al. . |
| Re. 30,922 | 5/1982 | Heilman et al. . |
| 3,105,839 | 10/1963 | Renner . |
| 3,236,705 | 2/1966 | Gilman et al. . |
| 3,236,808 | 2/1966 | Goldberg et al. . |
| 3,262,914 | 7/1966 | Goldberg et al. . |
| 3,265,708 | 8/1966 | Stiteler . |
| 3,267,081 | 8/1966 | Rudner et al. . |
| 3,313,783 | 4/1967 | Iwakura et al. . |
| 3,354,129 | 11/1967 | Edmonds et al. . |
| 3,355,272 | 11/1967 | D'Alessandro . |
| 3,386,969 | 6/1968 | Levine . |
| 3,408,349 | 10/1968 | Matsunaga . |
| 3,431,235 | 3/1969 | Lubowitz . |
| 3,435,003 | 3/1969 | Craven . |
| 3,449,442 | 6/1969 | Williams et al. . |
| 3,450,711 | 6/1969 | Megna et al. . |
| 3,453,236 | 7/1969 | Culbertson . |
| 3,454,673 | 7/1969 | Schmidt . |
| 3,458,486 | 7/1969 | Ray et al. . |

(List continued on next page.)

FOREIGN PATENT DOCUMENTS

| | | |
|---|---|---|
| 1175998 | 9/1984 | Canada . |
| 1269576 | 5/1990 | Canada . |
| 0152372 | 1/1985 | European Pat. Off. . |
| 0175484 | 3/1986 | European Pat. Off. . |
| 0067976 | 3/1987 | European Pat. Off. . |
| 0289695 | 1/1988 | European Pat. Off. . |
| 0283636 | 1/1988 | European Pat. Off. . |
| 0277476 | 8/1988 | European Pat. Off. . |
| 0292434 | 11/1988 | European Pat. Off. . |
| 0289798 | 11/1988 | European Pat. Off. . |
| 0292677 | 11/1988 | European Pat. Off. . |
| 0266662 | 11/1988 | European Pat. Off. . |
| 0294555 | 12/1988 | European Pat. Off. . |
| 0132547 | 2/1989 | European Pat. Off. . |
| 0305882 | 3/1989 | European Pat. Off. . |
| 0309649 | 4/1989 | European Pat. Off. . |
| 0310735 | 4/1989 | European Pat. Off. . |
| 0311735 | 4/1989 | European Pat. Off. . |
| 0317754 | 5/1989 | European Pat. Off. . |
| 0323540 | 7/1989 | European Pat. Off. . |

(List continued on next page.)

OTHER PUBLICATIONS

St. Clair, et al., *Additives Lower Pickup of Moisture by Polyimides* NASA Tech Briefs, 80–81 Apr., 1989.

Heidemann, "*Oligomers*" Encyclopedia of Polymer Science and Technology vol. 9 Molding to Petroleum Resins 485–506 1968.

*Second-generation polyimide raises continuous-use temperatures* Advanced Composites May/Jun., 1988.

Vanucci et al., *700° F. Properties of Autoclave Cured PMR–II Composites* NASA Tech. Memo 100923 Sep., 1988.

Vanucci, *PMR Polyimide Compositions for Improved Performance at 371° C.* NTIS N87–16071 Apr., 1987.

Elsenbaumer et al., *Highly Conductive Meta Derivatives of Poly (phenylene Sulfide)* J. Polymer Sci: Polymer Phys. Ed., vol. 20, 1781–1787 1982.

Patel et al., *Poly–Schiff Bases, I. Preparation of Poly–Schiff Bases from 4,4'–Diacetyl Diphenyl Ether (DDE) with Various Diamines* J. of Polymer Sci: Polymer Chem. Ed., vol. 20, 1985–1992 1982.

(List continued on next page.)

*Primary Examiner*—Richard L. Raymond
*Attorney, Agent, or Firm*—John C. Hammar

[57] ABSTRACT

Multidimensional oligomers of the present invention are surprisingly useful for advanced composites because each generally has a use temperature greatly in excess of its curing temperature. The oligomers have essentially no arms, and comprise crosslinking phenylimide end caps condensed directly onto an aromatic hub (preferably, phenyl) through "commodity" polymeric linkages, such as amide, diimide, ether, or ester. For example, p-nadicimidobenzoylchloride can be condensed with triaminobenzene to yield a multidimensional, crosslinking amide oligomer. Short chains of ether/carbonyl aromatic chains can be included, if desired. Methods for making these high-performance oligomers with ether/carbonyl aromatic chains use an Uhlman ether synthesis followed by a Friedel-Crafts reaction.

10 Claims, No Drawings

U.S. PATENT DOCUMENTS

| | | |
|---|---|---|
| 3,461,461 | 8/1969 | Anthony et al. . |
| 3,528,950 | 9/1970 | Lubowitz . |
| 3,530,087 | 9/1970 | Hayes et al. . |
| 3,536,670 | 10/1970 | Aeiony et al. . |
| 3,562,223 | 2/1971 | Bargain et al. . |
| 3,563,951 | 2/1971 | Dormagen et al. . |
| 3,565,549 | 2/1971 | Lubowitz et al. . |
| 3,592,841 | 7/1971 | Broadhead . |
| 3,598,768 | 8/1971 | Bach . |
| 3,609,181 | 9/1971 | Lubowitz et al. . |
| 3,616,193 | 10/1971 | Lubowitz et al. . |
| 3,624,042 | 11/1971 | Lubowitz et al. . |
| 3,631,222 | 12/1971 | Vogel . |
| 3,632,428 | 1/1972 | Lubowitz et al. . |
| 3,635,891 | 1/1972 | Lubowitz et al. . |
| 3,641,207 | 2/1972 | Lauchlan . |
| 3,647,529 | 3/1972 | Lubowitz et al. . |
| 3,652,710 | 3/1972 | Holub . |
| 3,658,764 | 4/1972 | Bargain et al. . |
| 3,658,938 | 4/1972 | Kwiatkowski et al. . |
| 3,663,507 | 5/1972 | Vogel . |
| 3,689,464 | 9/1972 | Holub et al. . |
| 3,697,308 | 10/1972 | Lubowitz . |
| 3,697,345 | 10/1972 | Lubowitz et al. . |
| 3,699,074 | 10/1972 | Lubowitz et al. . |
| 3,699,075 | 10/1972 | Lubowitz et al. . |
| 3,708,370 | 1/1973 | Lubowitz et al. . |
| 3,708,439 | 1/1973 | Sayigh et al. . |
| 3,708,459 | 1/1973 | Lubowitz . |
| 3,729,446 | 4/1973 | Holub et al. . |
| 3,745,149 | 7/1973 | Serafini et al. . |
| 3,748,311 | 7/1973 | Burns et al. . |
| 3,748,312 | 7/1973 | Burns et al. . |
| 3,749,735 | 7/1973 | Loria . |
| 3,757,088 | 9/1973 | Osborn . |
| 3,759,777 | 9/1973 | Lubowitz . |
| 3,761,441 | 9/1973 | D'Alessandra et al. . |
| 3,763,101 | 10/1973 | Jones et al. . |
| 3,770,697 | 11/1973 | Holub et al. . |
| 3,772,250 | 11/1973 | Economy et al. . |
| 3,773,718 | 11/1973 | Klebe et al. . |
| 3,781,240 | 12/1973 | Lubowitz et al. . |
| 3,781,249 | 12/1973 | Lubowitz . |
| 3,803,081 | 4/1974 | Lubowitz . |
| 3,812,159 | 5/1974 | Lubowitz . |
| 3,827,927 | 8/1974 | Lubowitz et al. . |
| 3,839,287 | 10/1974 | Kwiatkowski et al. . |
| 3,843,593 | 10/1974 | Shell et al. . |
| 3,847,867 | 11/1974 | Heath et al. . |
| 3,847,869 | 11/1974 | Williams, III . |
| 3,853,815 | 12/1974 | Lubowitz . |
| 3,859,252 | 1/1975 | Cho . |
| 3,879,349 | 4/1975 | Bilow et al. . |
| 3,879,393 | 4/1975 | Havera . |
| 3,879,428 | 4/1975 | Heath et al. . |
| 3,887,582 | 6/1975 | Holub et al. . |
| 3,890,272 | 6/1975 | D'Alelio . |
| 3,895,064 | 7/1975 | Brode et al. . |
| 3,896,147 | 7/1975 | Stephen . |
| 3,897,395 | 7/1975 | D'Alelio . |
| 3,909,507 | 9/1975 | Betts et al. . |
| 3,914,334 | 10/1975 | Lubowitz et al. . |
| 3,919,177 | 11/1975 | Campbell . |
| 3,920,768 | 11/1975 | Kwiatkowski . |
| 3,925,324 | 12/1975 | Gerard . |
| 3,933,862 | 1/1976 | Williams, III . |
| 3,935,167 | 1/1976 | Marvel et al. . |
| 3,935,320 | 1/1976 | Chiu et al. . |
| 3,941,746 | 3/1976 | Stephen . |
| 3,956,320 | 5/1976 | Heath et al. . |
| 3,957,732 | 5/1976 | Hirooka et al. . |
| 3,957,862 | 5/1976 | Heath et al. . |
| 3,966,678 | 6/1976 | Gruffaz et al. . |
| 3,966,726 | 6/1976 | Toth et al. . |
| 3,966,987 | 6/1976 | Suzuki et al. . |
| 3,970,714 | 7/1976 | Bargain . |
| 3,972,902 | 8/1976 | Heath et al. . |
| 3,988,374 | 10/1976 | Brode et al. . |
| 3,993,630 | 11/1976 | Darmory et al. . |
| 3,998,786 | 12/1976 | D'Alelio . |
| 4,000,146 | 12/1976 | Gerber . |
| 4,005,134 | 1/1977 | Markezich . |
| 4,013,600 | 3/1977 | Cassat . |
| 4,020,069 | 4/1977 | Johnson et al. . |
| 4,026,871 | 5/1977 | D'Alelio . |
| 4,038,261 | 7/1977 | Crouch et al. . |
| 4,051,177 | 9/1977 | Braden et al. . |
| 4,055,543 | 10/1977 | D'Alelio . |
| 4,058,505 | 11/1977 | D'Alelio . |
| 4,060,515 | 11/1977 | D'Alelio . |
| 4,064,289 | 12/1977 | Yokoyama et al. . |
| 4,075,171 | 2/1978 | D'Alelio . |
| 4,097,456 | 6/1978 | Barie . |
| 4,100,137 | 7/1978 | Lemieux et al. . |
| 4,100,138 | 7/1978 | Bilow et al. . |
| 4,101,488 | 7/1978 | Ishizuka et al. . |
| 4,107,147 | 8/1978 | Williams, III et al. . |
| 4,107,153 | 8/1978 | Akijama et al. . |
| 4,107,174 | 8/1978 | Baumann et al. . |
| 4,108,837 | 8/1978 | Johnson et al. . |
| 4,108,926 | 8/1978 | Arnold et al. . |
| 4,111,879 | 9/1978 | Mori et al. . |
| 4,115,231 | 9/1978 | Darms et al. . |
| 4,115,362 | 9/1978 | Inata et al. . |
| 4,116,937 | 9/1978 | Jones et al. . |
| 4,124,593 | 11/1978 | Gschwend et al. . |
| 4,126,619 | 11/1978 | Darms et al. . |
| 4,128,574 | 12/1978 | Markezich et al. . |
| 4,132,715 | 1/1979 | Roth . |
| 4,132,716 | 1/1979 | Kvita et al. . |
| 4,134,895 | 1/1979 | Roth et al. . |
| 4,142,870 | 3/1979 | Lovejoy . |
| 4,158,731 | 6/1979 | Baumann et al. . |
| 4,166,168 | 8/1979 | D'Alelio . |
| 4,167,663 | 9/1979 | Granzow et al. . |
| 4,168,366 | 9/1979 | D'Alelio et al. . |
| 4,172,836 | 10/1979 | Baumann et al. . |
| 4,174,326 | 11/1979 | Baumann et al. . |
| 4,175,175 | 11/1979 | Johnson et al. . |
| 4,176,223 | 11/1979 | Irwin . |
| 4,179,551 | 12/1979 | Jones et al. . |
| 4,183,839 | 1/1980 | Gagliani . |
| 4,187,364 | 2/1980 | Darms et al. . |
| 4,189,560 | 2/1980 | Roth et al. . |
| 4,193,927 | 3/1980 | Baumann et al. . |
| 4,197,397 | 4/1980 | D'Alelio et al. . |
| 4,200,731 | 4/1980 | Massey et al. . |
| 4,206,106 | 6/1980 | Heilman et al. . |
| 4,218,555 | 8/1980 | Antonoplos et al. . |
| 4,221,895 | 9/1980 | Woo . |
| 4,225,497 | 9/1980 | Baudouin et al. . |
| 4,225,498 | 9/1980 | Baudouin et al. . |
| 4,231,934 | 11/1980 | Oba et al. . |
| 4,234,712 | 11/1980 | Keller et al. . |
| 4,237,262 | 12/1980 | Jones . |
| 4,239,883 | 12/1980 | Stenzenberger . |
| 4,244,853 | 1/1981 | Serafini et al. . |
| 4,250,096 | 2/1981 | Kvita et al. . |
| 4,251,417 | 2/1981 | Chow et al. . |
| 4,251,418 | 2/1981 | Chow et al. . |
| 4,251,419 | 2/1981 | Heilman et al. . |
| 4,251,420 | 2/1981 | Antonoplos et al. . |

| | | | | | |
|---|---|---|---|---|---|
| 4,255,313 | 3/1981 | Antonoplos et al. . | 4,562,231 | 12/1985 | Dean . |
| 4,266,047 | 5/1981 | Jablonski et al. . | 4,562,232 | 12/1985 | Smith . |
| 4,269,961 | 5/1981 | Jones et al. . | 4,563,498 | 1/1986 | Lucas . |
| 4,271,079 | 6/1981 | Maeda et al. . | 4,563,514 | 1/1986 | Liu et al. . |
| 4,273,916 | 6/1981 | Jones . | 4,564,553 | 1/1986 | Pellegrini et al. . |
| 4,276,407 | 6/1981 | Bilow et al. . | 4,567,216 | 1/1986 | Qureshi et al. . |
| 4,288,583 | 9/1981 | Zahir et al. . | 4,567,240 | 1/1986 | Hergenrother et al. . |
| 4,288,607 | 9/1981 | Bier et al. . | 4,568,737 | 2/1986 | Tomalia et al. . |
| 4,289,699 | 9/1981 | Oba et al. . | 4,574,144 | 3/1986 | Yates et al. . |
| 4,293,670 | 10/1981 | Robeson et al. . | 4,574,148 | 3/1986 | Wicker, Jr. et al. . |
| 4,297,472 | 10/1981 | Heiss . | 4,574,154 | 3/1986 | Okamoto et al. . |
| 4,297,474 | 10/1981 | Williams et al. . | 4,576,857 | 3/1986 | Gannett et al. . |
| 4,298,720 | 11/1981 | Yamazaki et al. . | 4,577,034 | 3/1986 | Durvasula . |
| 4,299,750 | 11/1981 | Antonoplos et al. . | 4,578,433 | 3/1986 | Muenstedt et al. . |
| 4,299,946 | 11/1981 | Balme et al. . | 4,578,470 | 3/1986 | Webb . |
| 4,302,575 | 11/1981 | Takekoshi . | 4,584,364 | 4/1986 | Lubowitz et al. . |
| 4,323,662 | 4/1982 | Oba et al. . | 4,587,329 | 5/1986 | Tomalia et al. . |
| 4,338,222 | 7/1982 | Limburg et al. . | 4,590,363 | 5/1986 | Bernard . |
| 4,338,225 | 7/1982 | Sheppard . | 4,599,383 | 7/1986 | Satoji . |
| 4,344,869 | 8/1982 | Blinne et al. . | 4,600,769 | 7/1986 | Kumar et al. . |
| 4,344,870 | 8/1982 | Blinne et al. . | 4,604,437 | 8/1986 | Renner . |
| 4,351,932 | 9/1982 | Street et al. . | 4,608,414 | 8/1986 | Kitsunai et al. . |
| 4,358,561 | 11/1982 | Keske et al. . | 4,608,426 | 8/1986 | Stern . |
| 4,360,644 | 11/1982 | Naarmann et al. . | 4,611,022 | 9/1986 | Hefner, Jr. . |
| 4,365,068 | 12/1982 | Darms et al. . | 4,611,048 | 9/1986 | Peters . |
| 4,375,427 | 3/1983 | Miller et al. . | 4,614,767 | 9/1986 | Dean . |
| 4,376,710 | 3/1983 | Gardos et al. . | 4,615,832 | 10/1986 | Kress et al. . |
| 4,381,363 | 4/1983 | Reinhart . | 4,616,070 | 10/1986 | Zeiner et al. . |
| 4,389,504 | 6/1983 | St. Clair et al. . | 4,616,071 | 10/1986 | Holubka . |
| 4,393,188 | 7/1983 | Takahashi et al. . | 4,617,390 | 10/1986 | Hoppe et al. . |
| 4,395,497 | 7/1983 | Naarmann et al. . | 4,624,888 | 11/1986 | St. Clair et al. . |
| 4,400,613 | 8/1983 | Popelish . | 4,628,067 | 12/1986 | Chen, Sr. et al. . |
| 4,405,770 | 9/1983 | Schoenberg et al. . | 4,628,079 | 12/1986 | Zecher et al. . |
| 4,407,739 | 10/1983 | Naarmann et al. . | 4,629,777 | 12/1986 | Pfeifer . |
| 4,409,382 | 10/1983 | Keller . | 4,631,337 | 12/1986 | Tomalia et al. . |
| 4,410,686 | 10/1983 | Hefner, Jr. et al. . | 4,638,027 | 1/1987 | Mark et al. . |
| 4,414,269 | 11/1983 | Lubowitz et al. . | 4,640,944 | 2/1987 | Brooks . |
| 4,417,039 | 11/1983 | Reinhardt et al. . | 4,649,080 | 3/1987 | Fischer et al. . |
| 4,417,044 | 11/1983 | Parekh . | 4,654,410 | 3/1987 | Kashiwame et al. . |
| 4,418,181 | 11/1983 | Monacelli . | 4,657,973 | 4/1987 | Endo et al. . |
| 4,423,202 | 12/1983 | Choe . | 4,657,977 | 4/1987 | Peters . |
| 4,429,108 | 1/1984 | Stephens . | 4,657,987 | 4/1987 | Rock et al. . |
| 4,438,273 | 3/1984 | Landis . | 4,657,990 | 4/1987 | Daoust et al. . |
| 4,438,280 | 3/1984 | Monacelli . | 4,660,057 | 4/1987 | Watanabe et al. . |
| 4,446,191 | 5/1984 | Miyadera et al. . | 4,661,604 | 4/1987 | Lubowitz et al. . |
| 4,448,925 | 5/1984 | Hanson . | 4,663,378 | 5/1987 | Allen . |
| 4,460,783 | 7/1984 | Nishikawa et al. . | 4,663,399 | 5/1987 | Peters . |
| 4,465,809 | 8/1984 | Smith . | 4,663,423 | 5/1987 | Yamada et al. . |
| 4,467,011 | 8/1984 | Brooks et al. . | 4,663,424 | 5/1987 | Stix et al. . |
| 4,476,184 | 10/1984 | Lubowitz et al. . | 4,663,425 | 5/1987 | Evers et al. . |
| 4,476,295 | 10/1984 | Stephens . | 4,680,326 | 7/1987 | Leland et al. . |
| 4,482,683 | 11/1984 | Quella et al. . | 4,680,377 | 7/1987 | Matsumura et al. . |
| 4,485,140 | 11/1984 | Gannett et al. . | 4,684,714 | 8/1987 | Lubowitz et al. . |
| 4,485,231 | 11/1984 | Landis . | 4,690,972 | 9/1987 | Johnson et al. . |
| 4,489,027 | 12/1984 | St. Clair et al. . | 4,691,025 | 9/1987 | Domeier et al. . |
| 4,504,632 | 3/1985 | Holub et al. . | 4,694,064 | 9/1987 | Tomalia et al. . |
| 4,507,466 | 3/1985 | Tomalia et al. . | 4,695,610 | 9/1987 | Egli et al. . |
| 4,510,272 | 4/1985 | Loszewski . | 4,699,975 | 10/1987 | Katto et al. . |
| 4,515,962 | 5/1985 | Renner . | 4,703,081 | 10/1987 | Blackwell et al. . |
| 4,519,926 | 5/1985 | Basalay et al. . | 4,708,983 | 11/1987 | Liang . |
| 4,520,198 | 5/1985 | D'Alelio et al. . | 4,709,004 | 11/1987 | Dai . |
| 4,526,838 | 7/1985 | Fujioka et al. . | 4,709,006 | 11/1987 | Tsai et al. . |
| 4,533,692 | 8/1985 | Wolfe et al. . | 4,709,008 | 11/1987 | Shimp . |
| 4,533,693 | 8/1985 | Wolfe et al. . | 4,714,768 | 12/1987 | Hemkielm et al. . |
| 4,533,724 | 8/1985 | Wolfe et al. . | 4,716,212 | 12/1987 | Gaughan . |
| 4,535,117 | 8/1985 | Mathis et al. . | 4,719,283 | 1/1988 | Bartmann . |
| 4,536,559 | 8/1985 | Lubowitz et al. . | 4,727,118 | 2/1988 | Egami . |
| 4,547,553 | 10/1985 | Lubowitz et al. . | 4,728,742 | 3/1988 | Renner . |
| 4,555,563 | 11/1985 | Hefner et al. . | 4,730,030 | 3/1988 | Hahn et al. . |
| 4,556,697 | 12/1985 | Curatolo et al. . | 4,737,550 | 4/1988 | Tomalia . |
| 4,556,705 | 12/1985 | McCready . | 4,739,030 | 4/1988 | Lubowitz et al. . |
| 4,558,120 | 12/1985 | Tomalia et al. . | 4,739,075 | 4/1988 | Odagiri et al. . |

| | | |
|---|---|---|
| 4,739,115 | 4/1988 | Byrd et al. . |
| 4,740,563 | 4/1988 | McCready et al. . |
| 4,740,564 | 4/1988 | McCready et al. . |
| 4,740,584 | 4/1988 | Shimp . |
| 4,742,166 | 5/1988 | Renner . |
| 4,748,227 | 5/1988 | Matzner et al. . |
| 4,755,584 | 7/1988 | Hanson et al. . |
| 4,755,585 | 7/1988 | Hanson et al. . |
| 4,757,118 | 7/1988 | Das et al. . |
| 4,757,128 | 7/1988 | Domb et al. . |
| 4,757,150 | 7/1988 | Guggenheim et al. . |
| 4,759,986 | 7/1988 | Marikar et al. . |
| 4,760,106 | 7/1988 | Gardner et al. . |
| 4,764,427 | 8/1988 | Hara et al. . |
| 4,766,180 | 8/1988 | Wong . |
| 4,766,197 | 8/1988 | Clendinning et al. . |
| 4,769,424 | 9/1988 | Takekoshi et al. . |
| 4,769,426 | 9/1988 | Iwasaki et al. . |
| 4,769,436 | 9/1988 | Beck et al. . |
| 4,774,282 | 9/1988 | Qureshi . |
| 4,777,208 | 10/1988 | Hefner, Jr. . |
| 4,778,830 | 10/1988 | Streu et al. . |
| 4,778,859 | 10/1988 | Ai et al. . |
| 4,778,898 | 10/1988 | Vonlanthen et al. . |
| 4,786,669 | 11/1988 | Dewhirst . |
| 4,786,685 | 11/1988 | Takida et al. . |
| 4,786,713 | 11/1988 | Rule et al. . |
| 4,798,685 | 1/1989 | Yaniger . |
| 4,798,686 | 1/1989 | Hocker et al. . |
| 4,798,882 | 1/1989 | Petri . |
| 4,801,676 | 1/1989 | Hisgen et al. . |
| 4,801,677 | 1/1989 | Eckhardt et al. . |
| 4,804,722 | 2/1989 | Hesse et al. . |
| 4,804,724 | 2/1989 | Harris et al. . |
| 4,806,407 | 2/1989 | Skinner et al. . |
| 4,808,717 | 2/1989 | Saito et al. . |
| 4,812,518 | 3/1989 | Haubennestel et al. . |
| 4,812,534 | 3/1989 | Blakely . |
| 4,812,552 | 3/1989 | Cliffton et al. . |
| 4,812,588 | 3/1989 | Schrock . |
| 4,814,416 | 3/1989 | Poll . |
| 4,814,417 | 3/1989 | Sugimori . |
| 4,814,421 | 3/1989 | Rosenquist . |
| 4,814,472 | 3/1989 | Lau . |
| 4,816,503 | 3/1989 | Cunningham et al. . |
| 4,816,526 | 3/1989 | Bristowe et al. . |
| 4,816,527 | 3/1989 | Rock . |
| 4,816,556 | 3/1989 | Gay et al. . |
| 4,820,770 | 4/1989 | Schleifstein . |
| 4,826,927 | 5/1989 | Schmid et al. . |
| 4,826,997 | 5/1989 | Kirchhoff . |
| 4,827,000 | 5/1989 | Schwartz . |
| 4,829,138 | 5/1989 | Barthelemy . |
| 4,835,197 | 5/1989 | Mercer . |
| 4,837,256 | 6/1989 | Gardner et al. . |
| 4,839,378 | 6/1989 | Koyama et al. . |
| 4,845,150 | 7/1989 | Kovak et al. . |
| 4,845,167 | 7/1989 | Alston et al. . |
| 4,845,185 | 7/1989 | Teramoto et al. . |
| 4,845,278 | 7/1989 | Erhan . |
| 4,847,333 | 7/1989 | Lubowitz et al. . |
| 4,851,280 | 7/1989 | Gupta . |
| 4,851,287 | 7/1989 | Hartsing, Jr. . |
| 4,851,494 | 7/1989 | Eldin et al. . |
| 4,851,495 | 7/1989 | Sheppard et al. . |
| 4,851,496 | 7/1989 | Poll et al. . |
| 4,851,501 | 7/1989 | Lubowitz et al. . |
| 4,851,505 | 7/1989 | Hayes . |
| 4,861,855 | 8/1989 | Bockrath et al. . |
| 4,861,882 | 8/1989 | Hergenrother et al. . |
| 4,861,915 | 8/1989 | Clendinning et al. . |
| 4,861,924 | 8/1989 | Riggs . |
| 4,868,270 | 9/1989 | Lubowitz et al. . |
| 4,871,475 | 10/1989 | Lubowitz et al. . |
| 4,874,834 | 10/1989 | Higashi et al. . |
| 4,876,325 | 10/1989 | Olson et al. . |
| 4,876,328 | 10/1989 | Lubowitz et al. . |
| 4,876,330 | 10/1989 | Higashi et al. . |
| 4,891,167 | 1/1990 | Clendinning et al. . |
| 4,891,408 | 1/1990 | Newman-Evans . |
| 4,891,460 | 1/1990 | Ishii et al. . |
| 4,895,892 | 1/1990 | Satake et al. . |
| 4,895,924 | 1/1990 | Satake et al. . |
| 4,897,527 | 1/1990 | Cripps et al. . |
| 4,902,335 | 2/1990 | Kume et al. . |
| 4,902,440 | 2/1990 | Takeyama et al. . |
| 4,902,769 | 2/1990 | Cassidy et al. . |
| 4,902,773 | 2/1990 | Bodnar et al. . |
| 4,916,210 | 4/1990 | Jackson . |
| 4,916,235 | 4/1990 | Tan et al. . |
| 4,919,992 | 4/1990 | Blundell et al. . |
| 4,923,752 | 5/1990 | Cornelia . |
| 4,927,899 | 5/1990 | Michaud et al. . |
| 4,927,900 | 5/1990 | Michaud et al. . |
| 4,931,531 | 6/1990 | Tamai et al. . |
| 4,931,540 | 6/1990 | Mueller et al. . |
| 4,935,523 | 6/1990 | Lubowitz et al. . |
| 4,958,031 | 9/1990 | Sheppard et al. . |
| 4,965,336 | 10/1990 | Lubowitz et al. . |
| 4,973,662 | 11/1990 | Odagiri et al. . |
| 4,980,481 | 12/1990 | Lubowitz et al. . |
| 4,981,922 | 1/1991 | Sheppard et al. . |
| 4,985,568 | 1/1991 | Lubowitz et al. . |
| 4,990,624 | 2/1991 | Sheppard et al. . |
| 4,996,101 | 2/1991 | Landis et al. . |
| 5,003,035 | 3/1991 | Tsai et al. . |
| 5,011,905 | 4/1991 | Lubowitz et al. . |
| 5,066,541 | 11/1991 | Lubowitz et al. . |
| 5,066,776 | 11/1991 | Russeler et al. . |
| 5,071,941 | 12/1991 | Lubowitz et al. . |
| 5,075,537 | 12/1991 | Lorenzen et al. . |
| 5,082,905 | 1/1992 | Lubowitz et al. . |
| 5,086,154 | 2/1992 | Camberlin et al. . |
| 5,087,701 | 2/1992 | Lubowitz et al. . |
| 5,104,967 | 4/1992 | Sheppard et al. . |
| 5,109,105 | 4/1992 | Lubowitz et al. . |
| 5,111,026 | 5/1992 | Ma . |
| 5,112,936 | 5/1992 | Okamoto . |
| 5,112,939 | 5/1992 | Lubowitz et al. . |
| 5,115,087 | 5/1992 | Sheppard et al. . |
| 5,116,935 | 5/1992 | Lubowitz et al. . |
| 5,120,819 | 6/1992 | Lubowitz et al. . |
| 5,126,410 | 6/1992 | Lubowitz et al. . |
| 5,144,000 | 9/1992 | Sheppard et al. . |
| 5,151,487 | 9/1992 | Lubowitz et al. . |
| 5,155,206 | 10/1992 | Lubowitz et al. . |
| 5,159,055 | 10/1992 | Sheppard et al. . |
| 5,175,233 | 12/1992 | Lubowitz et al. . |
| 5,175,234 | 12/1992 | Lubowitz et al. . |
| 5,175,304 | 12/1992 | Sheppard . |
| 5,198,526 | 3/1993 | Lubowitz et al. . |
| 5,210,213 | 5/1993 | Sheppard et al. . |
| 5,216,117 | 6/1993 | Sheppard et al. . |
| 5,227,461 | 7/1993 | Lubowitz et al. . |
| 5,230,956 | 7/1993 | Cole et al. . |
| 5,239,046 | 8/1993 | Lubowitz et al. . |
| 5,254,605 | 10/1993 | Kim et al. . |
| 5,268,519 | 12/1993 | Sheppard et al. . |
| 5,286,811 | 2/1994 | Lubowitz et al. . |
| 5,338,532 | 8/1994 | Tomalia et al. . |
| 5,344,894 | 9/1994 | Lubowitz . |
| 5,403,666 | 4/1995 | Lubowitz et al. ............... 428/474.4 |

FOREIGN PATENT DOCUMENTS

| | | |
|---|---|---|
| 0336856 | 10/1989 | European Pat. Off. . |
| 0405128 | 1/1991 | European Pat. Off. . |
| 0418406 | 3/1991 | European Pat. Off. . |
| 0334778 | 4/1992 | European Pat. Off. . |
| 7100975 | 1/1971 | France . |
| 2166209 | 8/1973 | France . |
| 2210635 | 7/1974 | France . |
| 2272119 | 12/1975 | France . |
| 2303818 | 10/1976 | France . |
| 1951632 | 5/1971 | Germany . |
| 1453625 | 12/1973 | Japan . |
| 58059-219 | 10/1981 | Japan . |
| 57-10011-1 | 6/1982 | Japan . |
| 1210-408-A | 2/1988 | Japan . |
| 1210408 | 8/1989 | Japan . |
| 907105 | 10/1962 | United Kingdom . |
| 1069061 | 5/1967 | United Kingdom . |
| 1099096 | 1/1968 | United Kingdom . |
| 2002378 | 2/1977 | United Kingdom . |
| 2002378B | 3/1982 | United Kingdom . |
| 81/01855 | 7/1981 | WIPO . |
| 84/04313 | 11/1984 | WIPO . |

OTHER PUBLICATIONS

Walton, *A New Conjugated Network Polymer as an Electrical Conductor and Thermally Stable Plastic* Am. Chem., Soc. Org. Coat Plast. Chem., vol. 42, 595–599 1980.

Lubowitz et al., *Novel High Temperature Matrix Materials* 1986.

Serafini et al., *Thermally Stable Polyimides from Solutions of Monomeric Reactants* Journal of Applied Polymer Science, vol. 16, pp. 905–915 1972.

Spillman et al., *Copolymers of Poly(Para-Phenylene Terephthalamide) Containing a Thermally Activated Cross-Linking* PMSE vol. 68, Spring Meetings 139–140 1993.

Radlmann, et al., *New Synthesis of Poly (ether Ketones). (44195h)* Chem. Abstracts vol. 72, 1970, p. 44187 1970.

Bryant, et al., *Synthesis and Properties of Phenylethynyl–Terminated Polyimides* Polymer PrePrints, vol. 34, No. 1, 566–567 Mar. 1993.

Crivello et al., *Polyimidothioether–Polysulfide Block Polymers* Polymer Sci., Polymer Chem. Ed., vol. 13, pp. 1819–1842 1975.

Frazer, *High Temperature Resistant Polymers* Interscience Publishers, John Wiley & Sons, Inc., 139–213 1968.

Mittal (ed), *Polyimides* Plenum Press, NY, vol. 1 & 2 (selected pages) 1984.

St. Clair et al., *The Development of Aerospace Polyimide Adhesives* Mittal (ed), Polyimides–Synthesis Characterization and Applications, Plenum Press, NY, vol. 2, pp. 977–1041 1973.

Serafini, et al., *A Review of Processable High Temperature Resistant Addition–type Laminating Resins* Mittal (ed), Polyimides–Synthesis, Characterization and Applications, Plenum Press, NY, vol. 1, pp. 89–95 1973.

Stenson, *Polycyanurates Find Applications; Their Chemistry Remains Puzzling* Science/Technology, 208 ACS National Meeting, Washington, D.C., C&EN Northeast News Bureau 30–31 Sep. 1984.Sutter, et al., *Easily Processable High–Temperature Polyimide* NASA Tech..Briefs (two pages) 1986.

Stoakley, et al., *Low–Dielectric–Constant Polyimide/Glass Composites* NASA Tech. Briefs p. 24 Apr. 1994.

Bartolotta, *Predicting Fatigue Lives of Metal–Matrix/Fiber Composites* NASA Tech Briefs pp. 28, 30 Apr. 1994.

Vannucci, et al., *Improved PMR Polyimides for Heat–Stable Laminates* NASA Tech Briefs pp. 30–31 Apr. 1994.

Bryant, et al., *Phenylethynyl End–Capping Reagents and Reactive Diluents* NASA Tech Briefs pp. 36–37 Apr. 1994.

Jensen, et al., *Phenylethynyl–Terminated Ploy(Arylene Ethers)* NASA Tech Briefs p. 37 Apr. 1994.

Buckley, et al., *Processable Polyimides for High Temperature Applications* 36th International SAMPE Symposium pp. 1172–1181 Apr. 1991.

Edwards, et al. *Constituents of the Higher Fungi. Part XIII.[1] 2–Arly–3–methoxymaleic Anhydrides from Pulvinic Acid Derivatives. A Convenient Method for Determination of Structure of Fungaland Lichen Pulvinic Acid Derivatives* Journal of the Chemical Society pp. 1538–1542 1973.

Morrison, et al., *"Reactions" and Hofmann degradation of amides* Organic Chemistry Second Edition pp. 591 and 735 1966.

Kwiatkowski, et al., *Thermosetting Diphenyl Sulfone–Based Malcimides* Journal of Polymer Science, vol. 13, pp. 961–972 1975.

Lyle, et al., *Polyarylene Ethers: Maleimides, Nadimides and Blends* The Interdisciplinary Symposium on Recent Advances in Polyimides and Other High Performance Polymers, San Diego, Calif. pp. K–1–K–7 Jan. 1990.

Roberts, et al., *Effect of Solution Concentration and Aging Conditions on PMR–15 Resin* SAMPE Journal, pp. 24–28, 213 Mar./Apr 1986.

Southcott, et al., *"The Development of Processable, Fully Imidized, Polyimides for High–Temperature Applications"* High Perform. Polym. 6, pp. 1–12, Printed in UK 1994.

March, Advanced Organic Chemistry: Reactions, Mechanisms and Structure, McGraw-Hill, N.Y. (1968) pp. 413, 414, & 500.

Worthy et al., Chem. & Eng'g News, Feb. 22, 1988, pp. 19–21.

Tomalia et al., *Polymer J.*, vol. 17, No. 1 (1988).

COMPOSITES MADE FROM MULTIDIMENSIONAL OLIGOMERS

REFERENCE TO RELATED APPLICATIONS

The present invention is a divisional of Ser. No. 08/038,750, filed Mar. 26, 1993, now U.S. Pat. No. 5,463,076, which is a division of Ser. No. 07/000,605, filed Jan. 5, 1987, now U.S. Pat. No. 5,210,213 and a continuation-in-part application of U.S. patent application Ser. No. 810,817, filed Dec. 17, 1985, abandoned; which itself was a continuation-in-part application of U.S. Ser. No. 726,258, filed Apr. 23, 1985, abandoned; which itself was a continuation-in-part of the following five United States Patent Applications:

(a) U.S. Ser. No. 519,394, filed Aug. 1, 1983, now abandoned; and (b) U.S. Ser. No. 673,229, filed Nov. 20, 1984 (now U.S. Pat. No. 4,584,364, issued Apr. 22, 1986), which itself was a continuation of U.S. Ser. No. 576,790, filed Feb. 6, 1984, now abandoned, which itself was a continuation-in-part application of U.S. Ser. No. 321,119, filed Nov. 13, 1981, now abandoned; and (c) U.S. Ser. No. 536,350, filed Sep. 27, 1983, now abandoned, which itself was a continuation-in-part application of U.S. Ser. No. 519,394, filed Aug. 1, 1983, now abandoned; and (d) U.S. Ser. No. 505,348, filed Jun. 17, 1983, now U.S. Pat. No. 4,536,559; and (e) U.S. Ser. No. 651,826, filed Sep. 18, 1984, abandoned, which is a continuation-in-part application of the following three U.S. patent applications:

U.S. patent application Ser. No. 536,350, filed Sep. 27, 1983, abandoned, which itself was a continuation-in-part application of U.S. patent application Ser. No. 519,394, filed Aug. 1, 1983, abandoned;

U.S. patent application Ser. No. 576,790, filed Feb. 6, 1984, abandoned, which itself was a continuation-in-part application of U.S. patent application Ser. No. 321,119, filed Nov. 13, 1981, abandoned; and U.S. patent application Ser. No. 505,348, filed Jun. 17, 1983, now U.S. Pat. No. 4,536,559.

TECHNICAL FIELD

The present invention relates to multidimensional oligomers that include a hub and a plurality of radiating arms, each arm terminating at the periphery in a crosslinking end cap moiety. Such compounds have relatively low molecular weight, but cure to high performance composites useful at high temperatures.

BACKGROUND ART

Epoxies dominate the composite industry today primarily because they are relatively low-cost and are easy to use. Epoxies, however, have low thermal stabilitites and tend to be brittle. There is a need for high performance, temperature-resistant composites made curing inexpensive, "commodity" starting materials that will be useful in conditions where epoxies cannot be used. The present invention describes oligomers that fulfill these requirements and present great promise for engineering composites, particularly for aerospace applications.

SUMMARY OF THE INVENTION

Composites possessing glass transition temperatures greatly in excess of their curing temperatures can be prepared from multidimensional oligomers formed by the condensation of "commodity" starting materials. The oligomers have the general formula:

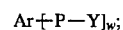

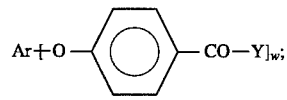

or

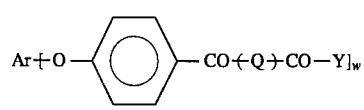

wherein w=an integer greater than 2 and not greater than the available number of substitutable hydrogens on the Ar group;

Ar=an aromatic moiety;

P=amide, ether, ester, or

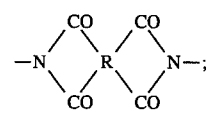

Y=

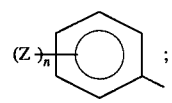

n=1 or 2;

Z=

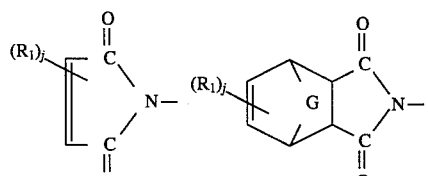

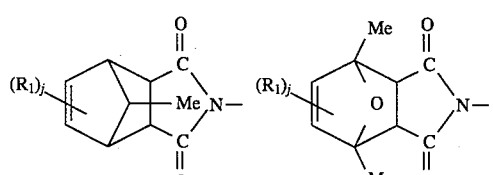

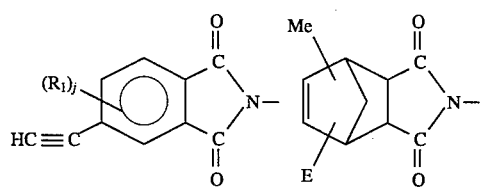

R=an organic radical having a valence of four;

$R_1$=any of lower alkyl, lower alkoxy, aryl, phenyl, or substituted aryl (including hydroxyl or halo-substituents);

j=0, 1, or 2;

E=allyl or methallyl;

G=—$CH_2$—, —S—, —O—, or —$SO_2$—;

Q=an organic radical of valence two, and preferably a compound selected from the group consisting of:

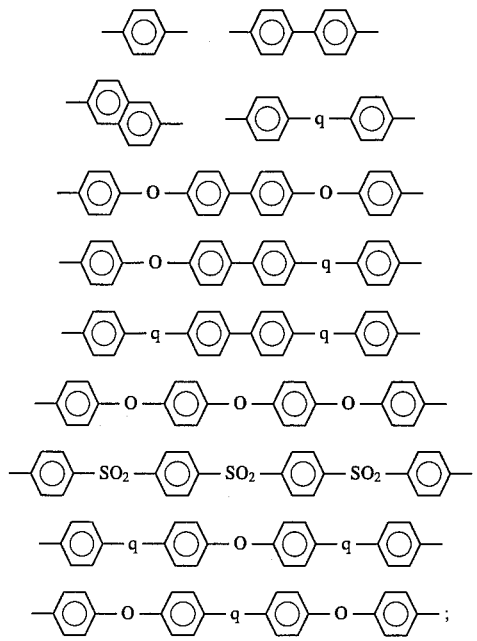

q=—$SO_2$—, —CO—, —S—, or —$(CF_3)_2C$—, and preferable —$SO_2$— or —CO—.

As will be explained, these oligomers are prepared by the condensation of an aromatic hub and a suitable end cap moeity with or without a chain-extending group (Q) to provide short-armed, multidimensional oligomers of high thermal stability.

BEST MODE CONTEMPLATED FOR MAKING AND USING THE INVENTION

Multidensional morphologies in crosslinking oligomers produce composites having solvent resistance, high glass transition temperatures, and toughness upon curing. The resins and prepregs are readily processed prior to curing. The cured composites have glass transition temperatures (melt temperatures) in excess of their curing temperatures. Such compounds can be readily made from "commodity" starting materials that are readily available at relatively low cost. The composites are cost competitive with epoxies, but possess better physical properties for aerospace applications (especially higher use temperatures).

Particularly perferred oligomers of the present invention have the general formula:

Ar+P—Y]$_w$;

wherein

Ar=an aromatic radial;

Y=a crosslinking end cap;

w=an integer greater than 2 and not greater than the available number of substitutable hydrogens on the Ar group;

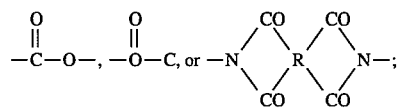

and

R=an organic radical having a valency of four, and, preferably, a residue of pyromellitic dianhydride, benzophenonetetracarboxylic dianhydride, or 5-(2,4-diketotetrahydrofuryl)-3-methyl-3-cyclohexene-1,2-dicarboxylic anhydride The crosslinking end cap (Y) is preferably a phenylimide having a formula:

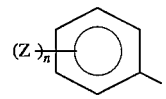

wherein n=1 or 2:

Z =

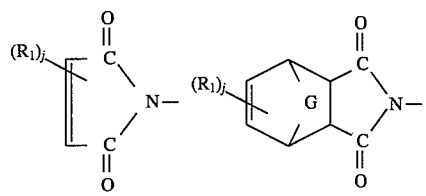

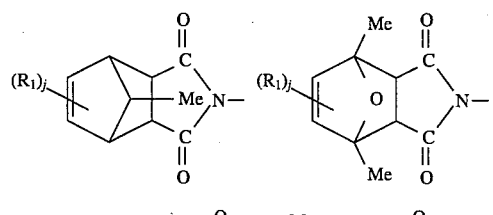

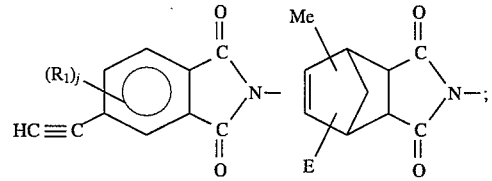

$R_1$=any of lower alkyl, lower alkoxy, aryl, or substituted aryl (including hydroxyl or halo- on any replaceable hydrogen);

j=0, 1, or 2; and

G=—$CH_2$—, —S—, —O—, or —$SO_2$—.

The most preferred end caps include:

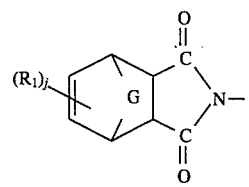

or

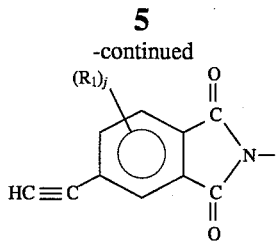

wherein
n=1 of 2 (preferably 2);
j=0, 1, or 2 (preferably 1);
G and $R_1$ are as previously defined (with $R_1$ preferably being

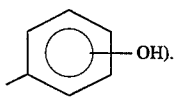

These multidimensional oligomers are made by the condensation of aromatic hub monomers with the end cap reactants in an inert atmosphere. For example, the hub might be

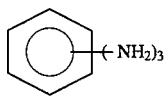

and the end cap, a radical as illustrated above terminated with an acid halide to form an amide linkage (NHCO) between the hub and the end cap. Alternatively, the hub might include the acid halide and the end cap the amine so that the condensation will yield an amide of opposite orientation (CONH). Ester or ether multidimensional oligomers of this general type are made in accordance with Examples I through VII of our application U.S. Ser. No. 810,817, now abandoned, by reacting an acid halide and a phenol. Diimide linkages are formed by reacting an amine-terminated hub with a dianhydride and an amine-terminated end cap.

The hub (Ar) precursor preferably is selected from the group consisting of phenyl, naphthyl, biphenyl, azalinyl (including melamine radicals) amines or acid halides, or triazine derivatives described in U.S. Pat. No. 4,574,154 (incorporated by reference) to Okamoto of the general formula:

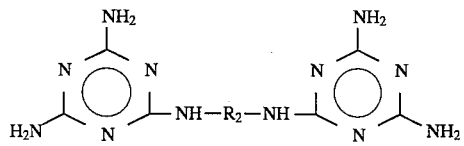

wherein $R_2$ is a divalent hydrocarbon residue containing 1–12 carbon atoms (and, preferably, ethylene).

Substantially stoichiometric amounts of the reactants are usually mixed together in a suitable solvent under an inert atmosphere to achieve the condensation. The reaction mixture may be heated, as necessary, to complete the reaction. Any of the oligomers can be used to form prepregs by application of the oligomers in a suitable solvent to suitable prepregging materials, and the prepregs can be cured in conventional vacuum bagging techniques at elevated temperatures to produce composites that have use temperatures in excess of their cure temperatures. The crosslinking end caps apparently bind the composites into a complex, 3-dimensional network upon curing by chemical induction or heating to yield a product having high thermal stability than the core temperature.

Compounds of the formulae:

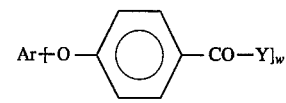

or

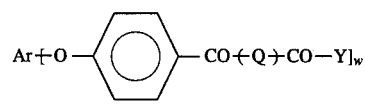

can also be synthesized with an Ullmann ether synthesis followed by a Friedel-Crafts reaction, as will be further explained.

Here, Q=

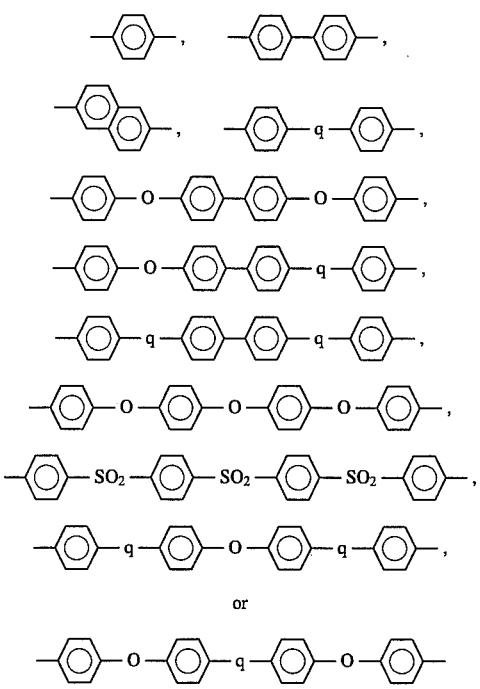

wherein q=—$SO_2$—, —CO—, —S—, or —$(CF_3)_2C$—, and preferably —$SO_2$— or —CO—.

To form the

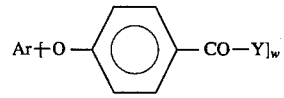

compounds, preferably a halo-substituted hub is reacted with phenol in DMAC with a base (NaOH) over a Cu Ullmann catalyst to produce an ether "star" with active hydrogens para- to the either linkages. End caps terminated with acid halide functionalities can react with these active aryl groups in a Friedel-Crafts reaction to yield the desired product. For example, 1 mole of trichlorobenzene can be reacted with about 3 moles of phenol in the Ullmann ether reaction to yield an intermediate of the general formula:

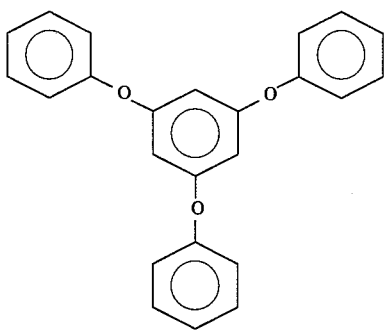

This intermediate can, then, be reacted with about 3 moles of (Y)-COCl to produce the final, crosslinkable, ether/carbonyl oligomer.

Similarly, to form the

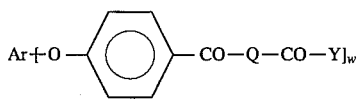

compounds, the hub is extended preferably by reacting a halo-substituted hub with phenol in the Ullmann ether synthesis to yield the ether intermediate of the

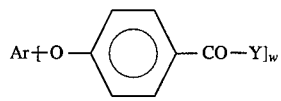

compounds. This intermediate is mixed with the appropriate stoichiometric amounts of a diacid halide of the formula XOC-Q-COX and an end cap of the formula

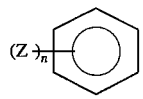

in the Friedel-Crafts reaction to yield the desired, chain-extended ether/carbonyl star and star-burst oligomers.

The end caps (Z) crosslink at different temperatures (i.e., their unsaturation is activated at different curing temperatures), so the cap should be selected to provide cured composites of the desired thermal stability. That is the backbone of the oligomer should be stable to at least the cure temperature of the caps. The multidimensional morphology allows the oligomers to be cured at a temperature far below the use temperature of the resulting composite, so completely aromatic backbones connected by heteroatoms are preferred to enhance the thermal stability.

U.S. Pat. No. 4,604,437 is incorporated by reference. That patent describes a polymer made from substituted, unsaturated, bicyclic imides having end caps of the formula:

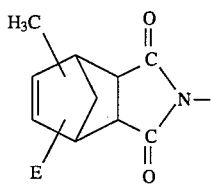

wherein
E=allyl or methallyl, and
n=1 or 2.

These bicyclic imide end caps are prepared from the analogous anhydride by condensation with an amine, and provide oligomers that cure in a temperature range between DONA (dimethyloxynadic) and nadic caps.

While essentially any dianhydride (aliphatic or aromatic can be used to form the diimide oligomers of the present invention, aromatic dianhydrides, such as pyromellitic dianhydride or benzophenonetetracarboxylic dianhydride, are preferred for cost, convenience, and thermal stability in the cured composite. If an aliphatic dianhydride is used, preferably the dianhydride is 5-(2,4-diketotetrahydrofuryl)-3-methyl-3-cyclohexene-1,2-dicarboxylic anhydride (MCTC).

End caps of the formula

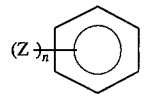

are prepared by reacting an amine-substituted benzene, such as aniline, with an anhydride in the manner outlined in U.S. Pat. No. 4,604,437. One process for making the precursor anhydrides is described in U.S. Pat. No. 3,105,839.

While preferred embodiments have been shown and described, those of oridinary skill in the art will recognize variation, modifications, or alterations that might be made to the embodiments that are described without departing from the inventive concept. Accordingly, the description should be interpreted liberally, and the claims should not be limited to the described embodiments, unless such limitation is necessary to avoid the pertinent prior art.

We claim:

1. A composite comprising fiber reinforcement and a matrix being a cured oligomer having a multidimensional morphology, the oligomer being selected form the group consisting of:

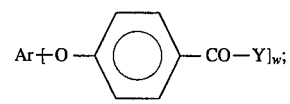

or

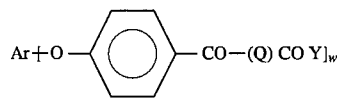

wherein

W=an integer greater than 2 and not greater than the available number of substitutable hydrogens on the Ar group;

Ar=phenylene, biphenylene, azalinylene, naphthylene, or a triazine derivative of the formula:

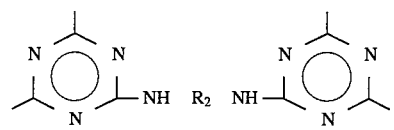

wherein
$R_2$=a divalent hydrocarbon residue containing 1–12 carbon atoms, and wherein, if Ar is a triazine derivative, P=NHCO—.

P=—NHCO—, —CONH—, —O—, —COO—, —OOC—, or

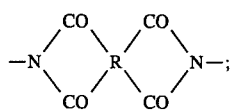

Y=

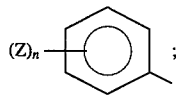

n=1 or 2;
Z=

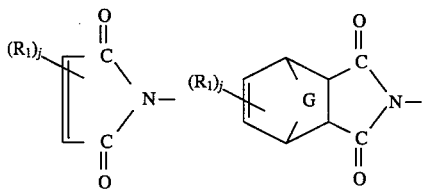

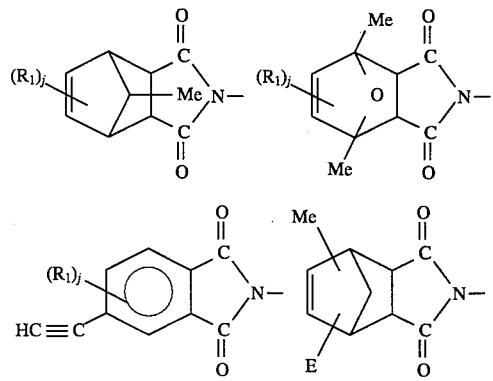

$R_1$=any of lower alkyl, lower alkoxy, aryl, or substituted aryl;
j=0, 1, or 2;
G=—$CH_2$—, —S—, —O—, or —$SO_2$—;
E=allyl or methallyl;
Q=a radical selected from the group consisting of:

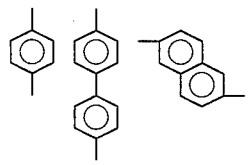

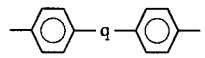

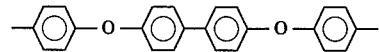

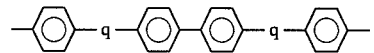

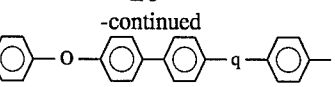

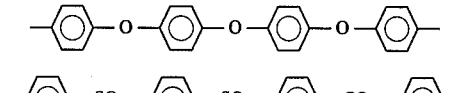

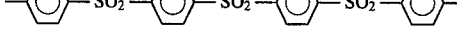

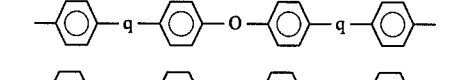

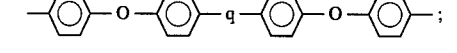

q=—$SO_2$—, —CO—, —S—, or —$(CF_3)_2C$—; and

R=a residue of a dianhydride, the dianhydride being selected from the group consisting of: pyromellitic dianhydride; benzophenonetetracarboxylic dianhydride; and 5-(2,4-diketotetrahydrofuryl)-3-methyl-3-cyclohexene-1,2-dicarboxylic anhydride.

2. The composite of claim 1 wherein the compound is selected from the group consisting of:

$$AR+P-Y]_w.$$

3. The composite of claim 1 wherein Ar is selected from the group consisting of phenylene, biphenylene, or azalinylene.

4. The composite of claim 1 wherein Ar is phenylene and w=3 or 4.

5. The composite of claim 5 wherein n=2.

6. The composite of claim 1 wherein the fiber reinforcement is a suitable fiber cloth.

7. The composite of claim 1 wherein Y includes a nadic functionality.

8. The composite of claim 1 wherein Y is

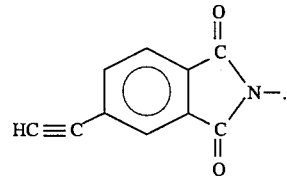

9. The composite of claim 1 wherein the oligomer has the formula:

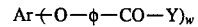

wherein Ø is phenylene.

10. The composite of claim 1 wherein the oligomer has the formula:

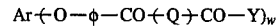

wherein Ø is phenylene.

* * * * *